US010286253B1

(12) United States Patent
Johnson

(10) Patent No.: US 10,286,253 B1
(45) Date of Patent: May 14, 2019

(54) RECIPROCATING DYNAMOMETER TO ASSESS HUMAN PHYSICAL CAPACITY AND MUSCLE COMPOSITION

(71) Applicant: Keith Emery Johnson, Aberdeen, NC (US)

(72) Inventor: Keith Emery Johnson, Aberdeen, NC (US)

( * ) Notice: Subject to any disclaimer, the term of this patent is extended or adjusted under 35 U.S.C. 154(b) by 0 days.

(21) Appl. No.: 15/180,123

(22) Filed: Jun. 13, 2016

Related U.S. Application Data

(63) Continuation-in-part of application No. PCT/US2015/066647, filed on Dec. 18, 2015.
(Continued)

(51) Int. Cl.
*A61B 5/22* (2006.01)
*A63B 21/00* (2006.01)
(Continued)

(52) U.S. Cl.
CPC .......... *A63B 24/0006* (2013.01); *A61B 5/221* (2013.01); *A61B 5/224* (2013.01);
(Continued)

(58) Field of Classification Search
CPC ......... A63B 22/00; A63B 21/00; A63B 24/00; A63B 21/00192; A63B 21/005;
(Continued)

(56) References Cited

U.S. PATENT DOCUMENTS

| 4,462,252 A | * | 7/1984 | Smidt | ................. A61B 5/1107 482/134 |
| 5,018,726 A | | 5/1991 | Yorioka | |

(Continued)

OTHER PUBLICATIONS

International Search Report PCT/US2015/066647 Related to Subject Application dated Apr. 15, 2016.
(Continued)

*Primary Examiner* — Loan B Jimenez
*Assistant Examiner* — Shila Jalalzadeh Abyaneh
(74) *Attorney, Agent, or Firm* — Nexsen Pruet, LLC; Michael A. Mann

(57) ABSTRACT

A reciprocating dynamometer assesses human physical capacity and muscle composition by: (1) simultaneously working all four limbs of the body through a full range of motion while maximally loading the muscles through a full range of speeds; (2) simultaneously capturing the reciprocating torques and reciprocating angular velocities of all four reciprocating limbs, and (3) adjusting to provide similar ranges of motion for limb joints of human subjects of different body height and limb length. Levers provide synchronized, reciprocating, angular movements for handles and pedals while adjustable brakes oppose reciprocating motion during a 15 second test of maximal exertion. Measurements of elapsed time, torque input to each lever and angular displacement of each lever enable a plot of cyclical moving average of power over cycle frequency for each limb. Peak cyclical power is the maximal rate of work performed, averaged over one movement cycle. Cycle frequency at peak cyclical power is a noninvasive reflection of muscle composition (fiber typing). Fundamental to this device and method is use of moving averages based not on time, but on movement cycle.

1 Claim, 9 Drawing Sheets

Related U.S. Application Data

(60) Provisional application No. 62/099,268, filed on Jan. 2, 2015.

(51) Int. Cl.
| | | |
|---|---|---|
| *A63B 21/22* | (2006.01) | |
| *A63B 22/00* | (2006.01) | |
| *A63B 22/06* | (2006.01) | |
| *A63B 24/00* | (2006.01) | |
| *A63B 23/035* | (2006.01) | |
| *A61B 5/00* | (2006.01) | |
| *A61B 90/00* | (2016.01) | |

(52) U.S. Cl.
CPC ...... *A61B 5/7285* (2013.01); *A63B 21/00192* (2013.01); *A63B 21/159* (2013.01); *A63B 21/225* (2013.01); *A63B 21/4034* (2015.10); *A63B 21/4035* (2015.10); *A63B 21/4045* (2015.10); *A63B 22/0012* (2013.01); *A63B 22/0664* (2013.01); *A63B 23/03575* (2013.01); *A63B 24/0062* (2013.01); *A61B 2090/066* (2016.02); *A61B 2562/0261* (2013.01); *A63B 2024/0009* (2013.01); *A63B 2024/0065* (2013.01); *A63B 2220/54* (2013.01)

(58) Field of Classification Search
CPC . A63B 21/0053; A63B 21/0056; A63B 23/00; A63B 22/0002; A63B 23/12; A63B 22/0007; A63B 21/001; A63B 22/0076; A63B 22/0012; A63B 22/0025; A63B 2022/003; A63B 2022/0033; A63B 2022/0035; A63B 2022/0041; A63B 2022/0043; A63B 22/0048; A63B 22/0056; A63B 2022/0092; A63B 2022/0094; A63B 22/06; A63B 22/0605; A63B 2022/0617; A63B 22/0664; A63B 2022/067; A63B 2022/0676; A63B 2022/206; A63B 23/035; A63B 23/03508; A63B 21/0726; A63B 21/0724; A63B 23/03516; A63B 23/03525; A63B 23/03523; A63B 23/3541; A63B 23/03575; A63B 23/04; A63B 23/0417; A63B 69/00; A63B 24/0062; A63B 2220/00; A63B 2220/10; A63B 2220/16; A63B 2220/50; A63B 2220/51; A63B 2220/54; A63B 2220/162; A63B 24/0006; A63B 21/159; A63B 21/225; A63B 21/4045; A63B 21/4034; A63B 21/4035; A63B 2024/0065; A63B 2024/0009; A61B 5/224; A61B 5/221; A61B 5/7285; A61B 2090/066; A61B 2562/0261

See application file for complete search history.

(56) References Cited

U.S. PATENT DOCUMENTS

| | | | | |
|---|---|---|---|---|
| 5,165,278 | A * | 11/1992 | Huszczuk | A61B 5/221 482/900 |
| 5,186,695 | A * | 2/1993 | Mangseth | A63B 21/0058 434/247 |
| 5,256,117 | A | 10/1993 | Potts et al. | |
| 5,277,674 | A * | 1/1994 | Tsuchiya | A61B 5/224 482/8 |
| 5,401,224 | A | 3/1995 | Tsuchiya et al. | |
| 5,569,120 | A | 10/1996 | Anjanappa et al. | |
| 5,695,431 | A | 12/1997 | Bond et al. | |
| 5,722,937 | A | 3/1998 | Smith | |
| 5,890,996 | A * | 4/1999 | Frame | A63B 21/154 482/111 |
| 2005/0049122 | A1 | 3/2005 | Vallone et al. | |
| 2006/0003873 | A1 * | 1/2006 | Kobayashi | A63B 21/005 482/92 |
| 2009/0017993 | A1 * | 1/2009 | Khanicheh | A63B 21/0056 482/49 |
| 2009/0062698 | A1 * | 3/2009 | Einav | G06F 19/00 601/5 |
| 2017/0248420 | A1 * | 8/2017 | Fyfe | G01L 5/162 |

OTHER PUBLICATIONS

Written Opinion of the ISR PCT/US2015/066647 dated Apr. 15, 2016.

* cited by examiner

RECIPROCATING DYNAMOMETER TO ASSESS HUMAN PHYSICAL CAPACITY AND MUSCLE COMPOSITION

TECHNOLOGY FIELD

The technology field is exercise equipment and methods for use. In particular, the technology field relates to human physical performance measuring devices and methods.

BACKGROUND

Human physical capacity is the maximal ability of the body to perform physical work. It is the basis for all physical activity, but until now, has never been measured. To measure human physical capacity would require a dynamometer capable of simultaneously working all four limbs of the body through a full range of motion while maximally loading the muscles through a full range of speeds, but until now, no such dynamometer existed.

Conventional dynamometers measure torque and angular velocity of rotating devices like automobile engines in order to calculate power (torque×angular velocity=power). But human limbs don't rotate; they reciprocate in an angular manner and to measure them would require a dynamometer capable of capturing the reciprocating torques and reciprocating angular velocities of reciprocating limbs. If, in addition, such a dynamometer was capable of adjusting to provide similar ranges of motion for limb joints of human users of different body height and limb length, a noninvasive reflection of muscle composition (fiber typing) would also be possible.

Such a dynamometer would express human physical capacity as the sum of the physical capacities of the four limbs, the physical capacity of each limb expressed as a plot of cyclical moving average of power (hereinafter called "cyclical power") over cycle frequency from which peak cyclical power and the corresponding cycle frequency at peak cyclical power would be identified. Peak cyclical power would be the maximal rate of work performed, averaged over one movement cycle. Cycle frequency at peak cyclical power would be a noninvasive reflection of muscle composition, revealing the unique blend of underlying, inheritable, yet trainable, metabolic energy pathways supporting the strength, speed and power of that limb. Fundamental to the expression of human physical capacity would be use of moving averages based not on time, but on movement cycle.

Such a dynamometer would: (1) identify peak cyclical power of the human body by simultaneously assessing the peak cyclical powers of the four limbs, providing a side by side comparison of left arm versus right arm, left leg versus right leg, left side of body versus right side of body, upper body versus lower body or the sum of all four limbs for a comparison involving the entire body; (2) identify cycle frequency at peak cyclical power for each limb as a noninvasive reflection of the muscle composition of that limb, revealing the unique blend of underlying, inheritable, yet trainable, metabolic energy pathways supporting the strength, speed and power of that limb; (3) establish normal ranges for peak cyclical power and the corresponding cycle frequency at peak cyclical power for specific human populations, with linear regressions for height, weight, age, sex, muscle composition, etc., for use in normalizing the impact of individual physical differences and enabling a meaningful discussion of a subject's current physical capacity and potential for improvement; (4) encourage new strength, speed and power research and thereby elevate anaerobic training to a level of credibility similar to aerobic training in the research literature; and (5) provide a safe, maximally intense, full range of motion and speed, exercise testing activity for individuals of any height, weight, age, sex, muscle composition, athletic ability, etc., and thereby enable them to witness the health benefits and structural and physiologic changes associated with strength, speed and power training.

With no such dynamometer and therefore no measure of human physical capacity, exercise research has been limited to aerobic testing despite the fact that aerobic capacity represents less than one third of human physical capacity. Nevertheless, the ability to measure oxygen uptake has given aerobic, cardiovascular endurance exercise a level of credibility well beyond that of anaerobic, strength, speed and power exercise even though sustained, repetitive, aerobic activities decrease flexibility, compromise lifesaving peripheral vascular and pulmonary reflexes, alter cardiac morphology to that seen in congestive heart failure and cause a disproportionate number of sudden cardiac deaths. Even the health benefits of aerobic exercise could be the result of unmeasured changes in strength, speed and power rather than changes in endurance. If available, a reciprocating dynamometer to assess human physical capacity and muscle composition would shed new light on these issues and add a new and long awaited perspective to this debate.

With no such dynamometer and therefore no noninvasive indicator of muscle composition, athletes have undergone muscle biopsies to determine their muscle compositions despite the damage done to otherwise healthy muscle tissue and the fact that muscle composition varies from muscle to muscle and limb to limb within the same individual. If available, a reciprocating dynamometer to assess human physical capacity and muscle composition would provide an alternative to muscle biopsies, namely, a plot of cyclical power over cycle frequency from which the corresponding cycle frequency at peak cyclical power would be identified for each limb, reflecting the muscle composition of that limb and unique blend of underlying, inheritable, yet trainable, metabolic energy pathways supporting the strength, speed and power of that limb.

With no such dynamometer, animal research using isolated muscle tissue preparations to study muscle physiology has had difficulty moving from theory to practice without a corresponding in vivo technique to study intact human muscles. If available, a reciprocating dynamometer to assess human physical capacity and muscle composition would demonstrate in maximally exercising human subjects, physiologic activity that, until now, has only been demonstrable in animal models.

With no such dynamometer, scholastic athletic programs have supported gifted athletes while less talented individuals become discouraged and drop out. If available, a reciprocating dynamometer to assess human physical capacity and muscle composition would introduce a new form of athletic competition in which a contestant's physical capacity test score is analyzed using linear regressions for height, weight, age, sex, muscle composition, etc., in order to normalize the impact of individual physical differences and statistically level the playing field so that anyone of any height, weight, age, sex, muscle composition, etc., could compete head to head with anyone else relative to their own physical potential and experience the challenge of reaching that potential.

With no such dynamometer, metabolic decline from youth to old age has been relentless, with progressive loss of strength, speed and power a recognized and sensitive biomarker of aging. If available, a reciprocating dynamometer to assess human physical capacity and muscle composition would challenge prevailing assumptions about exercise and aging, giving antiaging and longevity researchers a new technology with which to identify and combat causes and consequences of aging.

In summary, human physical capacity and muscle composition have eluded scientific measure because of an absence of dynamometers capable of: (1) simultaneously working all four limbs of the body through a full range of motion while maximally loading the muscles through a full range of speeds; (2) simultaneously capturing the reciprocating torques and reciprocating angular velocities of all four reciprocating limbs, and (3) adjusting to provide similar ranges of motion for limb joints of human subjects of different body height and limb length. As a result, advances in exercise physiology, healthcare, athletics and anti-aging/longevity research have been compromised. The present reciprocating dynamometer to assess human physical capacity and muscle composition addresses these issues.

The following works of others are hereby incorporated in their entirety by reference:
1. $2^{nd}$ Annual Duke Sports Cardiology & Sudden Death In Athletes Summit, Mar. 28, 2015, all presentations available on YouTube;
2. $1^{st}$ Annual Duke Sudden Cardiac Death In Athletes Symposium, Apr. 12, 2014, all presentations available on YouTube;
3. Exercise Physiology for Health, Fitness, and Performance, Fourth Edition, by Plowman and Smith (copyright 2014);
4. Physiology of Sport and Exercise, Fifth Edition, by Kenney, Wilmore and Costill (copyright 2012);
5. Olympic Textbook of Science in Sport, IOC, edited by Maughan (copyright 2009);
6. Strength and Power in Sport, Second Edition, IOC, edited by Komi (copyright 2003);
7. The Olympic Book of Sports Medicine, First Edition, IOC, edited by Dirix, Knuttgen and Tittel (copyright 1988);
8. Physiology of Exercise, Third Edition, by deVries (copyright 1980);
9. Textbook of Work Physiology, Second Edition, by Astrand and Rodahl (copyright 1977).

SUMMARY

A reciprocating dynamometer assesses human physical capacity and muscle composition by: (1) simultaneously working all four limbs of the body through a full range of motion while maximally loading the muscles through a full range of speeds; (2) simultaneously capturing the reciprocating torques and reciprocating angular velocities of all four reciprocating limbs, and (3) adjusting to provide similar ranges of motion for limb joints of human subjects of different body height and limb length. Levers provide synchronized, reciprocating; angular movements for handles and pedals while adjustable brakes oppose reciprocating motion during a 15 second test of maximal exertion. Measurements of elapsed time, torque input to each lever and angular displacement of each lever enable a plot of cyclical moving average of power over cycle frequency for each limb. Peak cyclical power is the maximal rate of work performed, averaged over one movement cycle. Cycle frequency at peak cyclical power is a noninvasive reflection of muscle composition (fiber typing). Fundamental to this device and method is use of moving averages based not on time, but on movement cycle.

The present reciprocating dynamometer to assess human physical capacity and muscle composition will contribute to our understanding of exercise physiology, healthcare, athletics and aging and thereby improve human health, vitality and longevity. Other features and advantages of this device and method will be apparent to those familiar with human physical performance testing and equipment from a careful reading of the Detailed Description accompanied by the drawings.

BRIEF DESCRIPTION OF THE DRAWINGS

In the figures.

DETAILED DESCRIPTION

Figure 1:
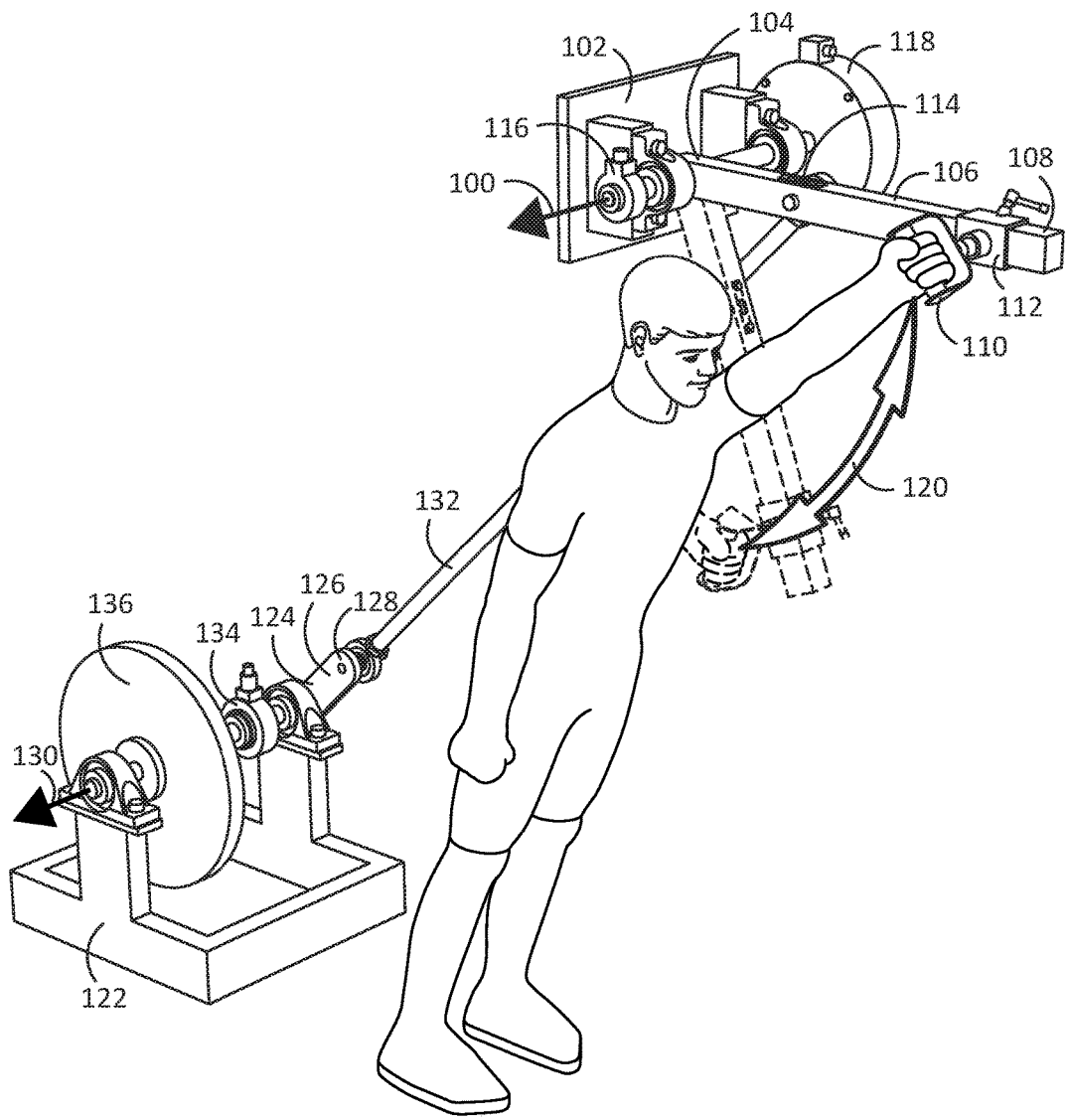
FIG. 1 is a perspective view of a simple embodiment of the present reciprocating dynamometer with one lever carrying an adjustable handle (or adjustable pedal) for use in providing similar ranges of motion for limb joints of human subjects of different body height and limb length, lever operationally connected to a strain gage, an absolute rotary encoder and a magnetic particle brake (or servo motor) for use in resisting reciprocating, angular movement of lever, lever operationally connected using a crank tie rod to a crank arm for use in providing uniform angular movements of lever from one movement cycle to the next, crank arm operationally connected to a secondary rotary encoder and a flywheel for use in assessing the physical capacity and muscle composition of one limb of a human subject.

Muscular activity requires energy and in the human body, energy comes from adenosine triphosphate (ATP). Three metabolic energy pathways are used to regenerate ATP in exercising muscle: (1) oxidative phosphorylation is inexhaustible, but slow, limiting aerobic metabolism to less than one third of maximal power; (2) anaerobic glycolysis is faster, but limited by lactic acidosis and fatigue to approximately 40 seconds of diminishing power; and (3) high-energy phosphates provide rapid energy from ATP and phosphocreatine for 8-10 seconds of maximal power.

These three metabolic energy pathways are represented by three corresponding muscle fiber types, each fiber type favoring a different pathway: (1) Type I fibers are rich in mitochondria for aerobic endurance; (2) Type IIa fibers favor anaerobic glycolysis for strength; and (3) Type IIx fibers favor high-energy phosphates for speed.

Fiber type, in turn, is determined by innervation: (1) Type I fibers are innervated by neurons with smaller diameter axons, lower excitation thresholds and slower conduction speeds; (2) Type IIa fibers are innervated by neurons with larger diameter axons, higher excitation thresholds and faster conduction speeds; and (3) Type IIx fibers are innervated by neurons with the largest diameter axons, highest excitation thresholds and fastest conduction speeds.

Whereas maximal force of contraction relative to cross-sectional area is similar for all three types of muscle fibers, maximal speed of contraction is specific for each fiber type, reflecting the favored metabolic energy pathway of that fiber: (1) Type I fibers exhibit slower maximal contraction speeds; (2) Type IIa fibers exhibit faster maximal contraction speeds; and (3) Type IIx fibers exhibit the fastest maximal contraction speeds.

During static (isometric) exercise, muscle fibers are recruited in a cumulative manner in ascending order (Type I→Type IIa→Type 11x) with increasing intensity of exertion such that during maximal exertion, all three fiber types are working maximally together. During dynamic exercise, ascending recruitment is overridden by the speed of contraction such that: (1) at slower contraction speeds, all three fiber types are available for recruitment; (2) at faster contraction speeds, only Type IIa and Type IIx fibers are available; and (3) at the fastest contraction speeds, only Type IIx fibers are recruited.

Over a lifetime, muscle fibers atrophy and are lost in descending order (Type IIx→Type IIa→Type I) due to lack of strength, speed and power exercise, malnutrition, disease, trauma, aging, etc., such that older, more debilitated people have fewer Type IIx and Type IIa fibers than younger, healthier people.

Muscle composition, the percentage of each fiber type within a muscle, is largely hereditary and unique to each person, providing a glimpse of that individual's genetic heritage and neuromuscular anatomy and physiology. Determining muscle composition (fiber typing), however, requires a muscle biopsy, an invasive procedure that damages otherwise healthy muscle tissue and which few healthy people are willing to undergo. The present reciprocating dynamometer to assess human physical capacity and muscle composition provides an alternative to muscle biopsies, namely, a plot of cyclical power over cycle frequency from which peak cyclical power and the corresponding cycle frequency at peak cyclical power are identified. Cycle frequency at peak cyclical power is a noninvasive reflection of muscle composition, revealing the unique blend of underlying, inheritable, yet trainable, metabolic energy pathways supporting that individual's strength, speed and power.

Muscle composition can vary from muscle to muscle and from limb to limb within the same individual making it desirable to identify the cycle frequency at peak cyclical power for each limb during a human physical capacity test. Simultaneous, independent measures of torque input and angular velocity for each limb enables distinguishing plots of data for a side by side comparison of the left arm versus right arm, left leg versus right leg, left side of the body versus right side of the body, upper body versus lower body or a composite of all four limbs for a comparison involving the entire body.

Human physical capacity testing reveals that: (1) people with predominately Type I muscle fibers generate plots of cyclical power over cycle frequency in which the peak cyclical power is skewed lower and to the left for endurance; (2) individuals with predominately Type IIa fibers generate plots of data in which the peak cyclical power is centered in the middle of the plot for strength; and (3) those with predominantly Type IIx fibers generate plots of data in which the peak cyclical power is skewed higher and to the right for speed. Youth and vitality test higher and to the right consistent with strength and speed; old age and debility test lower and to the left consistent with endurance after strength and speed are gone. All three metabolic energy pathways are trainable and changes can be monitored by serial testing using the present reciprocating dynamometer to assess human physical capacity and muscle composition.

Pooling human physical capacity test results from various populations enables the calculation of normal ranges for peak cyclical power and the corresponding cycle frequency at peak cyclical power, with linear regressions for height, weight, age, sex, muscle composition, etc., for use in normalizing the impact of individual physical differences and enabling a meaningful discussion of a subject's human physical capacity test results. Reference ranges are useful in gauging the present condition of a person's body and relative to other people with similar height, weight, age, sex, muscle composition, etc., their potential for improvement.

The validity of predicting an individual's physical potential based on human physical capacity testing depends on many factors, including: (1) the extent to which that individual's genetic potential was nurtured or neglected during childhood; (2) the extent to which their potential was positively or negatively influenced by sex hormones during puberty; (3) the extent to which their youthful development was maintained in adulthood or compromised due to lack of strength, speed and power exercise or malnutrition, disease, trauma, aging and psycho-social issues that can undermine even the best of potentials; and (4) the extent to which that individual is represented by the selected reference population. Regardless of these factors, measuring one's human physical capacity today is the first step toward recognizing and pursuing one's physical potential tomorrow.

Imagine a sporting event in which the opponent is not another contestant, but a machine, the present reciprocating dynamometer to assess human physical capacity and muscle composition. First, the machine adjusts for body height or limb length. Then each contestant performs a 15 second, full range of motion and speed, human physical capacity test. Linear regressions for height, weight, age, sex, muscle composition, etc., are applied to the test results to normalize the impact of individual physical differences and statistically level the playing field so that everyone has an equal chance to win. The real opponent, of course, is not the present reciprocating dynamometer, but a statistical projection of one's own physical potential and the real challenge is discovering how to reach that potential.

Previous attempts to measure anaerobic capacity in lieu of human physical capacity included the use of a bicycle ergometer and modified Wingate test. This method was limited and unpopular for several reasons: (1) the circular path of motion of the ergometer pedals failed to capture the reciprocating, angular power of the limbs; (2) the fixed length of the ergometer crank arms worked the joints of people with longer limbs through a smaller range of motion than the joints of people with shorter limbs; (3) test duration was 30 seconds or longer when peak cyclical power occurs within 10 seconds during maximal exertion; (4) total power was calculated as work/time and averaged over 3-5 second intervals rather than calculating power as torque×angular velocity and utilizing cyclical moving averages to generate plots of cyclical power over cycle frequency from which peak cyclical power and the corresponding cycle frequency at peak cyclical power could be identified; and (5) distinguishing the power of individual limbs was impossible using a bicycle ergometer.

To provide optimal and consistent ranges of motion for limb joints of human subjects of different body height and limb length, the present reciprocating dynamometer adjusts to increase or decrease the angular displacement of the levers to accommodate differences in limb length and raise or lower the arm lever axes relative to the leg lever axes to accommodate differences in body height. Pedals pivot about axes coaxial with the ankles rather than beneath the balls of the feet as with conventional bicycle pedals to minimize changes in mechanical advantage due to ankle flexion or extension.

The present reciprocating dynamometer to assess human physical capacity utilizes magnetic particle brakes or servo motors to generate brake torque output. Brake torque output is proportional to brake coil current and independent of speed and direction of rotation of the brake rotor. Brake torque output can be programmed to deliver a variety of brake profiles, including positive slopes, negative slopes, constant torques, hills and valleys, etc., not all of which are suitable for human physical capacity testing. However, since a variety of brake profiles could be used for purposes other than human physical capacity testing using the present reciprocating dynamometer, use of any and all brake profiles is included within the scope of this disclosure.

A human physical capacity test utilizing a brake profile having a positive slope proceeds as follows: A human subject identifies himself to the present reciprocating dynamometer's computer. The computer searches for previous test records for that subject and if found, automatically adjusts the arm lever axis height, lever angular displacement, brake profile and brake scaling factor according to the subject's previous personal best test performance. The subject then straps his feet into the pedals, grasps the handles and assumes a standing, slightly forward-leaning posture, moving the levers through their reciprocating, angular paths of motion to confirm or make further adjustments to the computer's automatic adjustments. When satisfied, a "READY" state is activated after which the subject takes a moment to gather his thoughts before explosively driving the handles and pedals through their reciprocating, angular movements as rapidly and forcefully as possible as servo motors (or magnetic particle brakes) increasingly resist and gradually slow the motion to a complete stop. The test lasts 15 seconds. Data acquisition starts automatically when the rapid movement begins and stops automatically when 15 seconds have elapsed. The subject then releases his feet from the pedals and steps away from the present reciprocating dynamometer to discuss his human physical capacity and muscle composition test results.

The brake scaling factor automatically adjusts to a subject's previous "personal best" test performance anticipating a similar performance on the current test. If a subject has no previous test record, the brake scaling factor is estimated according to their height, weight, age, sex, muscle composition, athletic ability, etc. If the current test performance is better than their previous personal best, the brake scaling factor is increased on their next test. If the current test performance is worse than their previous personal best, the brake scaling factor remains the same. A maximal physical effort generates a smooth plot of cyclical power over cycle frequency; a hesitant effort generates an erratic plot. A test duration longer than 15 seconds results in muscular fatigue before a true peak cyclical power can be achieved; a test duration less than 15 seconds reduces the calculation of peak cyclical power due to the nature of a moving average. Longer is not better; shorter is not better. Since a longer or shorter test duration could be used for purposes other than human physical capacity testing using the present reciprocating dynamometer, use of any and all test durations is included within the scope of this disclosure.

The defining expression of human physical capacity is a plot of cyclical power over cycle frequency from which peak cyclical power and the corresponding cycle frequency at peak cyclical power are identified for each limb. Applying a conventional moving average based on time to data obtained from accelerating or decelerating cyclical movements yields no meaningful results. Instead, a moving average based not on time, but on cycle length is applied to produce a plot of cyclical power over cycle frequency in which each data point represents an average of one movement cycle.

Use of a magnetic particle brake or servo motor manufacturer's published specification of brake torque output relative to brake coil current is insufficient for assessing human physical capacity and muscle composition. Therefore, a strain gage or reaction torque transducer is operationally connected to each lever to measure the torque input of each limb. Strain gages and reaction torque transducers require periodic calibration, but enable an unprecedented look at the power of each limb as all four limbs simultaneously deliver a maximal effort during a human physical capacity test.

Figure 6:
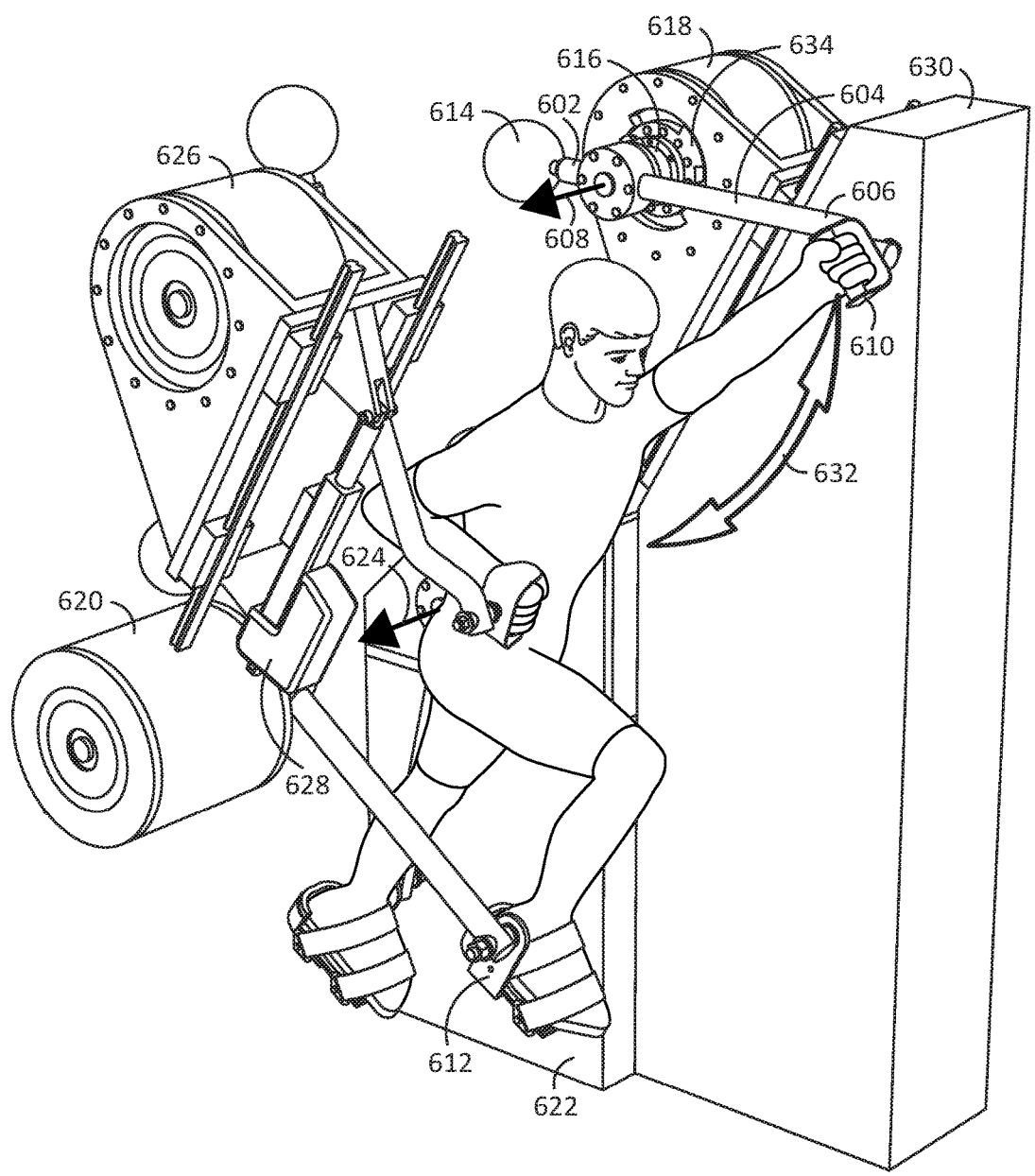
FIG. 6 is a perspective view of a different embodiment of the present reciprocating dynamometer with four levers, two levers carrying handles and two levers carrying pedals, each lever operationally connected to a reaction torque transducer operationally connected to a servo motor, each servo motor carrying a pedal rigidly mounted to a frame, each servo motor carrying a handle adjustably mounted to frame using an actuator for use in adjusting the height of the pivotal axis of lever to accommodate human subjects of different body height, frame on the right removed for clarity, all four servo motors operating in position mode and responsive to a position signal generated by a motion controller (see FIG. 8) operable to (1) simulate a master servo motor operating in velocity mode; (2) generate a position signal for use in adjusting and synchronizing opposing, angular movements of servo motors and corresponding levers for use in providing similar ranges of motion for limb joints of human subjects of different limb length; and (3) trigger capturing of data and generating of signals for use in simultaneously assessing physical capacities and muscle compositions of all four limbs of a human subject.

Electronic hardware used by the embodiment in FIG. 6 includes a motion controller operationally connected to four reaction torque transducers and four servo motors, each reaction torque transducer generating a torque input signal responsive to magnitude of torque applied to a corresponding lever, torque proportional to force applied by a human user to a corresponding handle or pedal for use in moving lever in a reciprocating, angular manner. Each servo motor operates in position mode and generates an encoder signal responsive to angular position of servo motor, angular position responsive to a position signal generated by motion controller.

Motion controller has a master timer, master timer generating a master timer signal, motion controller operable to: (1) simulate a master servo motor operating in velocity mode, master servo motor generating a master encoder signal responsive to master angular position of master servo motor, master angular position responsive to master angular velocity and master angular acceleration of master servo motor, master angular acceleration responsive to torque input signal and brake output signal; (2) generate position signal responsive to master encoder signal and body height input or limb length input of human user for use in adjusting and synchronizing opposing, angular movements of servo motors and corresponding levers for use in providing uniform angular movements of levers from one movement cycle to the next and providing similar ranges of motion for limb joints of human subjects of different body height and limb length; (3) use master encoder signal to trigger capturing of data derived from master timer signal, four torque input signals and four encoder signals and generating of brake output signal. Operationally connected to motion controller is a base computer (see FIG. 8).

Motion controller uses master encoder signal to trigger data acquisition. The first "Z" pulse following a "READY" indication starts data capture and then one row of data is stored for every "A" pulse. Therefore, a master encoder generating 360 pulses per revolution will trigger the capturing and storing of 360 rows of data for each push/pull movement cycle of the handles and pedals.

The motion controller stores data to internal memory during a test and uploads that data to a test data file in a database in a base computer following the test. Each test data file has a header which includes test date, time of day and user profile which includes user name, height, weight, birthdate, sex, arm lever axis height, lever angular displacement, brake profile, brake scaling factor and other distinguishing information such as Navy Seal, right hip replacement, etc.

Following the header are ten columns of data: (C1) row number, (C2) elapsed time in microseconds, (C3) torque—left arm in newton-meters, (C4) torque—right arm, (C5) torque—left leg and (C6) torque—right leg, (C7) position—left arm in radians, (C8) position—right arm, (C9) position—left leg, and (C10) position—right leg. These ten columns are for use in populating the first ten columns of a spreadsheet having a total of 32 columns, the remaining columns populated using the following computations:

(C11) incremental cycle frequency in cycles per second is computed as 1/(elapsed time less previous elapsed time);

(C12, C13, C14 and C15) incremental angular displacement in radians of each limb is computed as corresponding (C7, C8, C9, and C10) position less previous position;

(C16, C17, C18, and C19) incremental angular velocity in radians/second of each limb is computed as the product of corresponding (C12, C13, C14 and C15) incremental angular displacement and (C11) incremental cycle frequency;

(C20, C21, C22, and C23) incremental power in newton-meters per second of each limb is computed as the product of corresponding (C3, C4, C5 and C6) torque and corresponding (C16, C17, C18, and C19) incremental angular velocity.

The four torque columns, (C3, C4, C5 and C6) and four power columns (C20, C21, C22 and C23) each undergo cyclical moving averages. If the master encoder generates 360 pulses per revolution, a cyclical moving average is computed as (sum of data in rows 1-360)/360, then (sum of data in rows 2-361)/360, then (sum of data in rows 3-362)/360, etc., with cyclical moving average data recorded in the subsequent 8 columns starting on row 180 (the midpoint of the first cycle) and labeled: (C24) cyclical torque—left arm, (C25) cyclical torque—right arm, (C26) cyclical torque—left leg, (C27) cyclical torque—right leg, (C28) cyclical power—left arm, (C29) cyclical power—right arm, (C30) cyclical power—left leg and (C31) cyclical power—right leg.

(C32) cycle frequency in cycles per second is a data sequence computed as 1/(elapsed time in row 360 less elapsed time in row 1), then 1/(elapsed time in row 361 less elapsed time in row 2), then 1/(elapsed time in row 362 less elapsed time in row 3), etc., and recorded starting on row 180 of column (C32). The spreadsheet is now complete and ready for plotting and analysis.

Plotting options for the X axis include: (C1) row number, (C2) elapsed time, and (C32) cycle frequency. Plotting options for the Y axis include all 32 columns and in addition, torque, power, cyclical torque and cyclical power of left side of body, right side of body, upper body, lower body and total body.

Analysis includes identifying peak cyclical power and corresponding cycle frequency at peak cyclical power for each arm, each leg, left side of body, right side of body, upper body, lower body and total body. In addition, cyclical torque at cycle frequency of 1 cycle/second is a measure of strength and peak cycle frequency is a measure of speed.

FIG. 1 is a perspective view of a simple embodiment of the present reciprocating dynamometer with one lever carrying an adjustable handle (or adjustable pedal) for use in providing similar ranges of motion for limb joints of human subjects of different body height and limb length, lever operationally connected to a strain gage, an absolute rotary encoder and a magnetic particle brake (or servo motor) for use in resisting reciprocating, angular movement of lever, lever operationally connected using a crank tie rod to a crank arm for use in providing uniform angular movements of lever from one movement cycle to the next, crank arm operationally connected to a secondary rotary encoder and a flywheel for use in assessing the physical capacity and muscle composition of one limb of a human subject.

This embodiment comprises a frame 102. Pivotally mounted to frame 102 is the first end 104 of a lever 106 having first end 104 with pivotal axis 100 and a second end 108. Adjustably mounted to second end 108 of lever 106 is a handle 110 (or pedal) with a mounting bracket 112 for use in adjusting position of handle 110 along second end 108 of lever 106 closer to or farther from pivotal axis 100 of first end 104 of lever 106. Operationally connected to lever 106 is a strain gage 114 for use in generating torque input signal responsive to magnitude of torque applied to lever 106, torque proportional to force applied by a human subject to handle 110 for use in moving lever 106 in a reciprocating, angular manner 120. Operationally connected to lever 106 is an absolute rotary encoder 116 for use in generating an encoder signal responsive to angular position of lever 106. Operationally connected to lever 106 is a magnetic particle brake 118 (or servo motor) responsive to brake output signal to apply resistance to reciprocating, angular movement 120 of lever 106.

Rotatably mounted to a second aspect of the frame 122 is the first end 124 of a crank arm 126 having first end 124 with a rotational axis 130 and a second end 128. Operationally connected between lever 106 and second end 128 of crank arm 126 is a crank tie rod 132 for use in converting reciprocating, angular movement 120 of lever 106 to rotational movement of crank arm 126, crank arm 126 for use in providing uniform angular movements 120 of lever 106 from one movement cycle to the next. Operationally connected to crank arm 126 is a secondary rotary encoder 134 for use in generating a secondary encoder signal responsive to angular position of crank arm 126. Operationally connected to crank arm 126 is a flywheel 136 for use in smoothing the changes in direction of lever 106 at each end of its angular movement 120.

Operationally connected to strain gage 114, absolute rotary encoder 116, magnetic particle brake 118 and secondary rotary encoder 134 is a computer processor (not shown) having a timer, timer generating a timer signal, computer processor operable to use secondary encoder signal to trigger capturing of data derived from timer signal, torque input signal and encoder signal and generating of brake output signal such that data derived from these signals is based not on time, but on angular position of crank arm 126, thereby facilitating the subsequent calculations of cyclical moving averages. Data is uploaded to a base computer having a keyboard, mouse, video monitor and printer (see FIG. 8).

Figure 2:
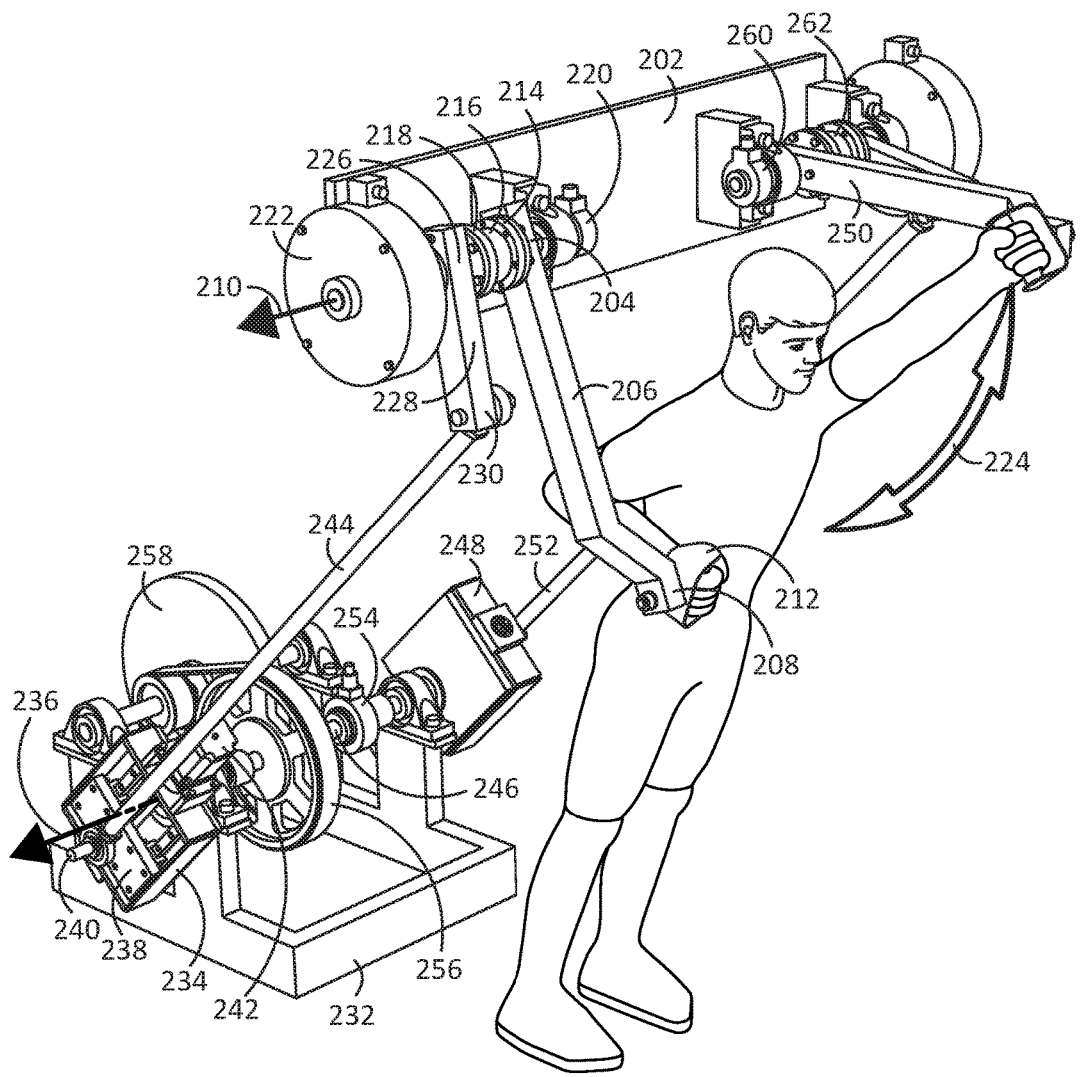
FIG. 2 is a perspective view of a different embodiment of the present reciprocating dynamometer with two levers carrying nonadjustable handles (or nonadjustable pedals), each lever operationally connected to a reaction torque transducer operationally connected to an absolute rotary encoder, a magnetic particle brake (or servo motor) and a crank drive lever, crank drive lever operationally connected using a crank tie rod to an adjustable crank assembly for use in adjusting angular movement of lever to provide similar ranges of motion for limb joints of human subjects of different body height and limb length, both adjustable crank assemblies operationally connected to a secondary rotary encoder and a belt and pulley driven flywheel for use in simultaneously assessing the physical capacities and muscle compositions of two limbs of a human subject.

FIG. 2 is a perspective view of a different embodiment of the present reciprocating dynamometer with two levers carrying nonadjustable handles (or nonadjustable pedals), each lever operationally connected to a reaction torque transducer operationally connected to an absolute rotary encoder, a magnetic particle brake (or servo motor) and a crank drive lever, crank drive lever operationally connected using a crank tie rod to an adjustable crank assembly for use in adjusting angular movement of lever to provide similar ranges of motion for limb joints of human subjects of different body height and limb length, both adjustable crank assemblies operationally connected to a secondary rotary encoder and a belt and pulley driven flywheel for use in simultaneously assessing the physical capacities and muscle compositions of two limbs of a human subject. This embodiment comprises all elements of the embodiment in FIG. 1 with the addition of two reaction torque transducers replacing the strain gage 114 in FIG. 1, two crank drive levers, two adjustable crank assemblies replacing the crank arm 126 in FIG. 1 and a belt and pulley driven flywheel.

This embodiment comprises a frame 202. Pivotally mounted to frame 202 is the first end 204 of a lever 206 having first end 204 with a pivotal axis 210 and a second end 208. Pivotally carried by second end 208 of lever 206 is a nonadjustable handle 212 (or nonadjustable pedal). Operationally connected and coaxial to first end 204 of lever 206 is the first end 214 of a reaction torque transducer 216 having first end 214, a second end 218 and a longitudinal axis 210, reaction torque transducer 216 for use in generating torque input signal responsive to magnitude of torque applied to lever 206, torque proportional to force applied by a human subject to nonadjustable handle 212 for use in moving lever 206 in a reciprocating, angular manner 224. Operationally connected to second end 218 of reaction torque transducer 216 is an absolute rotary encoder 220 for use in generating an encoder signal responsive to angular position of second end 218 of reaction torque transducer 216 and a magnetic particle brake 222 (or servo motor) responsive to brake output signal to apply resistance to reciprocating, angular movement 224 of lever 206. Operationally connected and coaxial to second end 218 of reaction torque transducer 216 is the first end 226 of a crank drive lever 228 having first end 226 with a pivotal axis 210 and a second end 230.

Rotatably mounted to a second aspect of the frame 232 is an adjustable crank assembly comprising a crank base 234 having a rotational axis 236, a crank table 238 having a stub shaft 240 with a longitudinal axis (not shown) and a crank actuator 242 for use in adjusting position of longitudinal axis of stub shaft 240 closer to or farther from rotational axis 236 of crank base 234. Operationally connected between stub shaft 240 and second end 230 of crank drive lever 228 is a crank tie rod 244 for use in converting reciprocating, angular movement 224 of crank drive lever 228 to rotational movement of adjustable crank assembly. Operationally connected and coaxial to crank base 234 is a crankshaft 246 having a longitudinal axis 236. Operationally connected and coaxial to crankshaft 246 is a second adjustable crank assembly 248 having a rotational axis 236 and oriented 180 degrees about longitudinal axis 236 of crankshaft 246 compared to crank base 234. Operationally connected between second adjustable crank assembly 248 and a second lever 250 is a second crank tie rod 252. Operationally connected to crankshaft 246 is a secondary rotary encoder 254 and a belt and pulley system 256 for use in increasing angular velocity and momentum of a flywheel 258.

Adjustable crank assembly 248 is for use in increasing or decreasing functional length of the crank arm, thereby increasing or decreasing angular movement 224 of second lever 250 for use in providing similar ranges of motion for limb joints of human subjects of different body height and limb length. Crank table 238 adjusts all the way down to "zero" crank arm length, where stub shaft 240 is coaxial to longitudinal axis 236 of crankshaft 246, thereby parking lever 206 in a neutral, stationary position suitable for shipping, aligning or calibrating. Operationally connecting both adjustable crank assemblies 248 to a common crankshaft 246 is for use in synchronizing opposing movements of lever 206 and second lever 250, enabling two arms (or two legs) to exercise simultaneously, one pushing while the other is pulling. Adjustable crank assemblies 248 are for use in providing uniform angular movements 224 of lever 206 and second lever 250 from one movement cycle to the next. Adjustable crank assembly 248 has a greater mass compared to crank arm 126 in FIG. 1, supplementing inertia of flywheel 258.

Operationally connecting absolute rotary encoder 220 to lever 206 and a second absolute rotary encoder 260 to second lever 250 is for use in distinguishing angular position of lever 206 from angular position of second lever 250. Operationally connecting reaction torque transducer 216 to lever 206 and a second reaction torque transducer 262 to second lever 250 is for use in distinguishing torque applied to lever 206 from torque applied to second lever 250.

Figure 3:
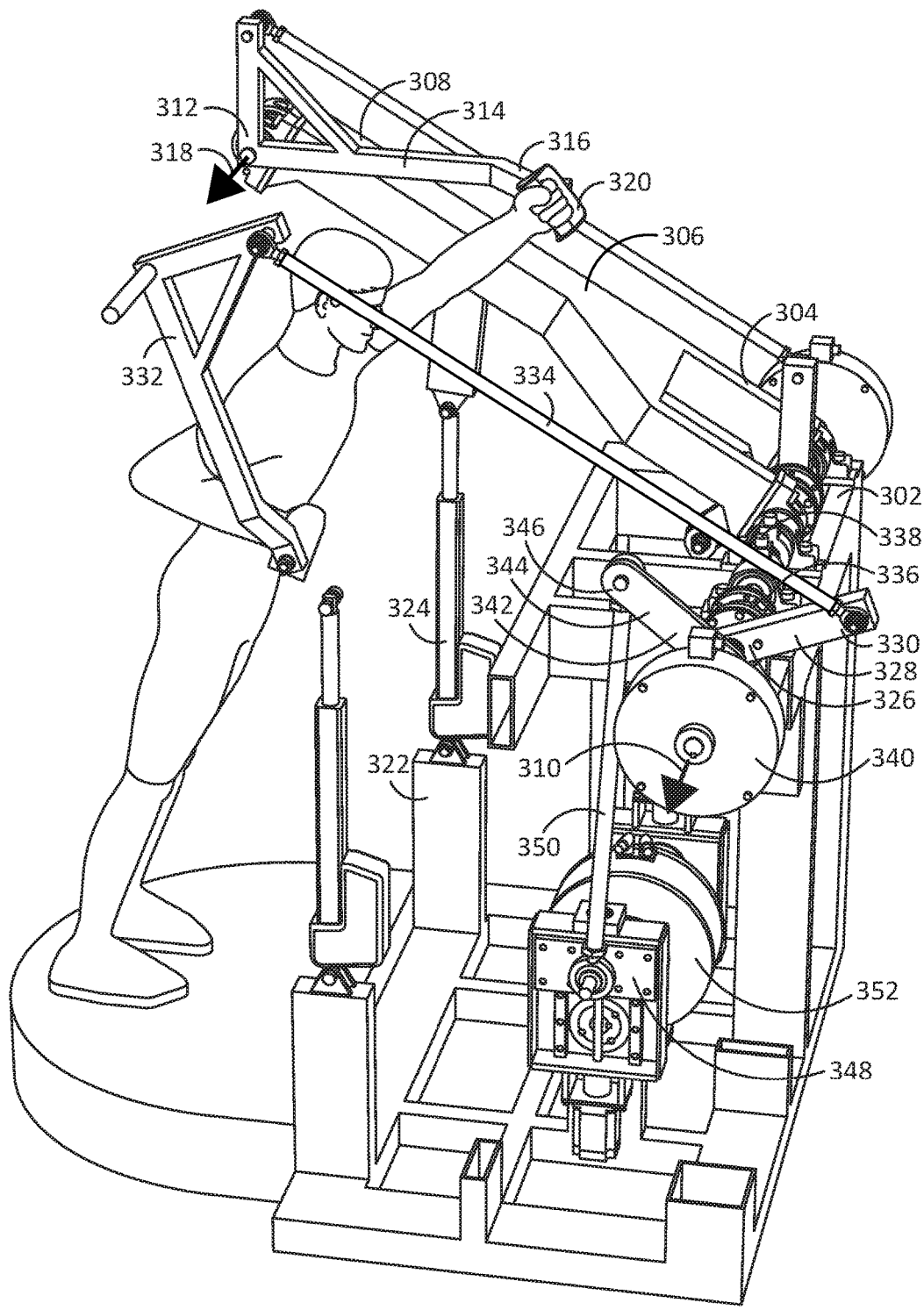
FIG. 3 is a perspective view of a different embodiment of the present reciprocating dynamometer with two accessory levers carrying handles, each accessory lever carried by a structural beam supported by an actuator for use in adjusting the height of the pivotal axis of the accessory lever to accommodate human subjects of different body height, accessory lever operationally connected using an accessory tie rod to a lever operationally connected to a reaction torque transducer operationally connected to an absolute rotary encoder, a magnetic particle brake (or servo motor) and a crank drive lever, crank drive lever operationally connected using a crank tie rod to an adjustable crank assembly, both adjustable crank assemblies operationally connected to a secondary servo motor operating in torque mode for use in counteracting inertia of reciprocating mechanical parts and simulating an adjustable flywheel for use in simultaneously assessing the physical capacities and muscle compositions of two limbs of a human subject.

FIG. 3 is a perspective view of a different embodiment of the present reciprocating dynamometer with two accessory levers carrying handles, each accessory lever carried by a structural beam supported by an actuator for use in adjusting the height of the pivotal axis of the accessory lever to accommodate human subjects of different body height, accessory lever operationally connected using an accessory tie rod to a lever operationally connected to a reaction torque transducer operationally connected to an absolute rotary encoder, a magnetic particle brake (or servo motor) and a crank drive lever, crank drive lever operationally connected using a crank tie rod to an adjustable crank assembly, both adjustable crank assemblies operationally connected to a secondary servo motor operating in torque mode for use in counteracting inertia of reciprocating mechanical parts and simulating an adjustable flywheel for use in simultaneously assessing the physical capacities and muscle compositions of two limbs of a human subject. This embodiment comprises all elements of the embodiment in FIG. 2 with the addition of two accessory levers, two structural beams, two actuators, two accessory tie rods and a secondary servo motor replacing the secondary rotary encoder 254, belt and pulley system 256 and flywheel 258 in FIG. 2.

This embodiment comprises a frame 302. Pivotally mounted to frame 302 are the first ends 304 of two structural beams 306, each structural beam 306 having first end 304 with a pivotal axis 310 and a second end 308, beam on the right removed for clarity. Pivotally mounted to second end 308 of structural beam 306 is the first end 312 of an accessory lever 314 having first end 312 with a pivotal axis 318 and a second end 316 carrying a handle 320. Supporting second end 308 of structural beam 306 and operationally connected between structural beam 306 and a second aspect of the frame 322 is an actuator 324 for use in raising or lowering second end 308 of structural beam 306 to adjust height of pivotal axis 318 of accessory lever 314 to accommodate human subjects of different body height.

Pivotally mounted to frame 302 and coaxial to pivotal axes 310 of first ends 304 of structural beams 306 are two levers 328, each lever 328 having a first end 326 with a pivotal axis 310 and a second end 330. Pivotally connected between second end 330 of lever 328 and a second accessory lever 332 is an accessory tie rod 334 for use in converting reciprocating, angular movement of second accessory lever 332 to reciprocating, angular movement of lever 328. Operationally connected and coaxial to first end 326 of lever 328 is a reaction torque transducer 336 having a longitudinal axis 310, reaction torque transducer 336 operationally connected to an absolute rotary encoder 338 and a magnetic particle brake 340. Operationally connected and coaxial to reaction torque transducer 336 is the first end 342 of a crank drive lever 344 having a first end 342 with a pivotal axis 310 and a second end 346. Operationally connected between second end 346 of crank drive lever 344 and an adjustable crank assembly 348 is a crank tie rod 350. Operationally connected to both adjustable crank assemblies 348 is a secondary servo motor 352 replacing the secondary rotary encoder 254, belt and pulley system 256 and flywheel 258 in FIG. 2, secondary servo motor 352 for use in generating secondary encoder signal, counteracting inertia of reciprocating mechanical parts and simulating an adjustable flywheel.

Figure 4:
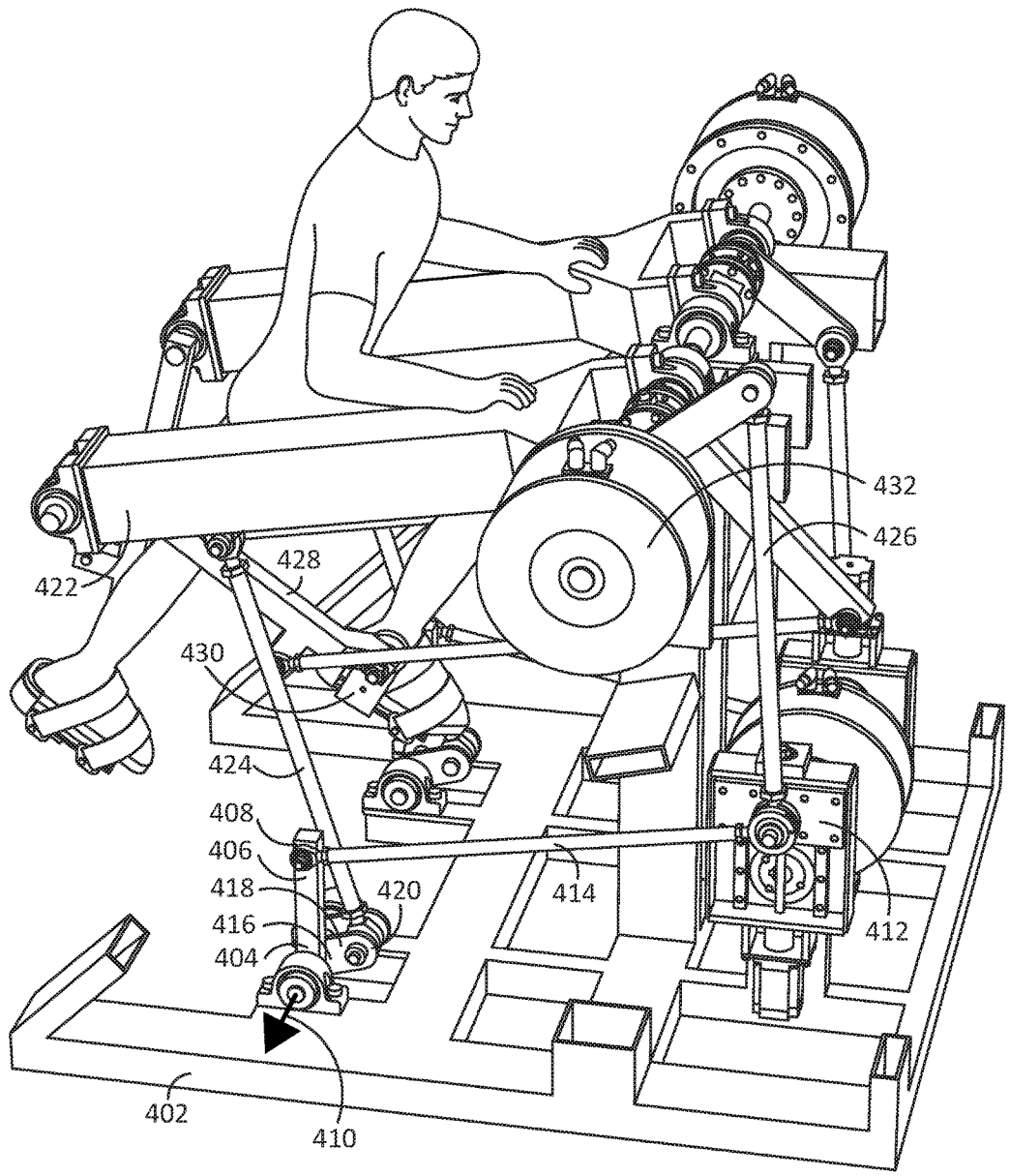
FIG. 4 is a perspective view of a different embodiment of the present reciprocating dynamometer with two accessory levers carrying pedals, each accessory lever carried by a structural beam supported by an elliptical assembly for use in generating an elliptical path of motion for the pedal, each accessory lever operationally connected to a servo motor (or magnetic particle brakes) operating in torque mode for use in resisting reciprocating, angular movement of accessory lever for use in simultaneously assessing the physical capacities and muscle compositions of two limbs of a human subject.

FIG. 4 is a perspective view of a different embodiment of the present reciprocating dynamometer with two accessory levers carrying pedals, each accessory lever carried by a structural beam supported by an elliptical assembly for use in generating an elliptical path of motion for the pedal, each accessory lever operationally connected to a servo motor (or magnetic particle brakes) operating in torque mode for use in resisting reciprocating, angular movement of accessory lever for use in simultaneously assessing the physical capacities and muscle compositions of two limbs of a human subject. This embodiment comprises all elements of the embodiment in FIG. 3 with the addition of two elliptical assemblies replacing the actuators 324 in FIG. 3, two servo motors replacing the absolute rotary encoders 338 and magnetic particle brakes 340 in FIG. 3 and two pedals replacing the handles 320 in FIG. 3.

This embodiment comprises a frame 402. Pivotally mounted to frame 402 are two elliptical assemblies, each elliptical assembly comprising an elliptical arm 406 having a first end 404 with a pivotal axis 410 and a second end 408. Operationally connected between second end 408 of elliptical arm 406 and a corresponding adjustable crank assembly 412 is an elliptical tie rod 414 for use in converting rotational movement of adjustable crank assembly 412 to reciprocating, angular movement of elliptical arm 406. Rigidly connected and coaxial to first end 404 of elliptical arm 406 is the first end 416 of a supporting arm 418 having first end 416 with a pivotal axis 410 and a second end 420. Pivotally connected between second end 420 of supporting arm 418 and a structural beam 422 is a supporting tie rod 424 for use in converting reciprocating, angular movement of supporting arm 418 to reciprocating, angular movement of structural beam 422.

Orienting the longitudinal axis of elliptical tie rod 414 at an angle of 90 degrees to the longitudinal axis of a crank tie rod 426 causes the reciprocating, angular movement of structural beam 422 to be 90 degrees out of phase with the reciprocating, angular movement of accessory lever 428. Rotating adjustable crank assembly 412 confirms that when accessory lever 428 is at either end of its angular movement, structural beam 422 is in the middle of its angular movement. Conversely, when structural beam 422 is at either end of its angular movement, accessory lever 428 is in the middle of its angular movement. The resulting elliptical path of motion of the pedal 430 feels more natural to an exercising human subject than a scissoring movement and removes the "dead spot" at each end of a scissoring movement. An elliptical path of motion does not increase or decrease peak cyclical power compared to a scissoring movement. Whereas legs prefer an elliptical path of motion, arms prefer a scissoring movement.

Legs are twice as strong as arms and require twice the brake torque output to resist the torque input of the legs in FIG. 4 as the arms in FIG. 3 and therefore require twice as many magnetic particle brakes as in FIG. 3 or two servo motors 432 operating in torque mode, each servo motor 432 capable of producing three times the brake torque output of one magnetic particle brake with the added benefits of having a built in absolute rotary encoder for use in generating encoder signal, faster response time and greater programmability.

Figure 5:
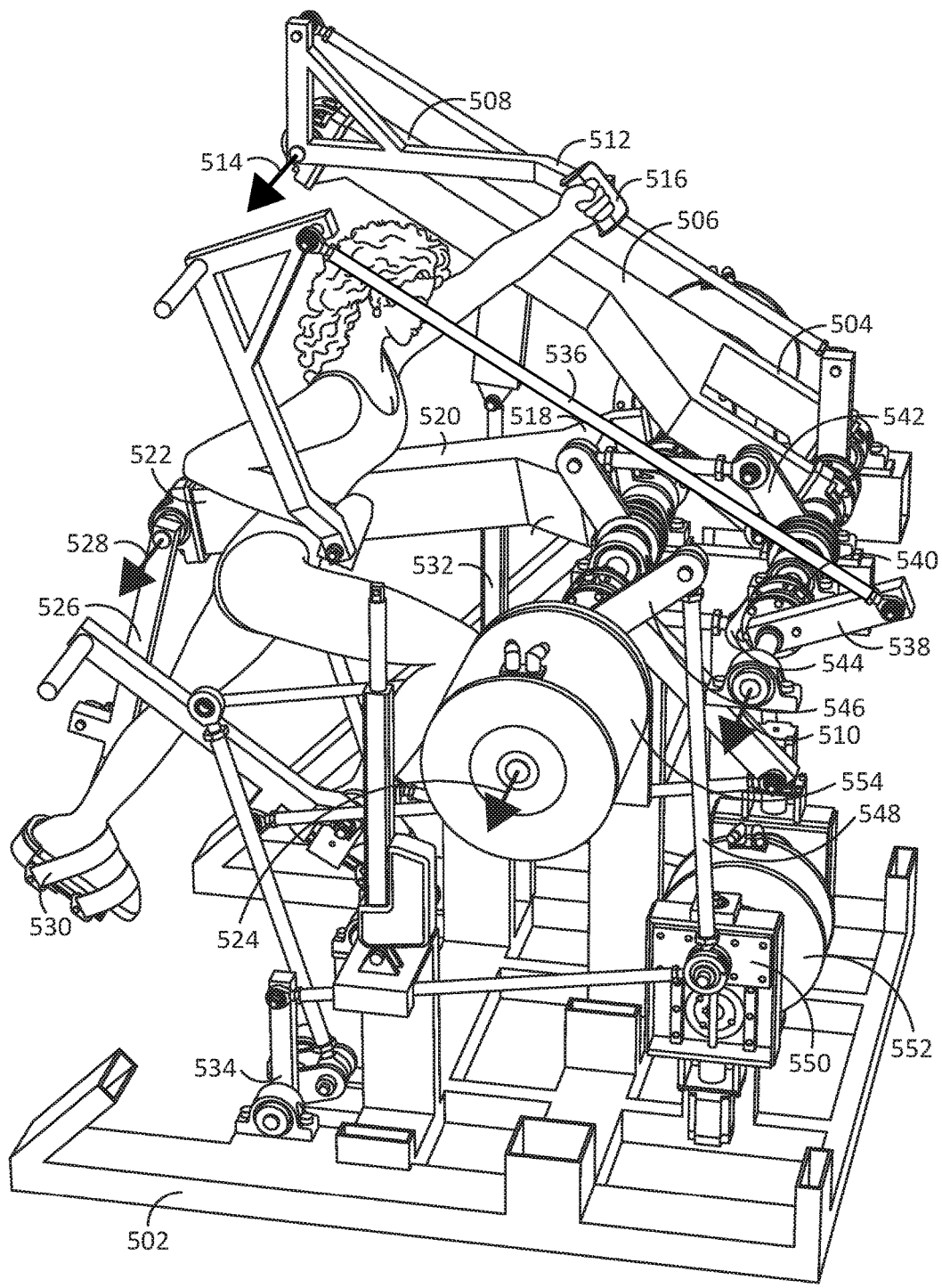
FIG. 5 is a perspective view of a different embodiment of the present reciprocating dynamometer with four accessory levers, two accessory levers carrying handles and two accessory levers carrying pedals, each accessory lever carrying a handle carried by a structural beam supported by an actuator for use in adjusting the height of the pivotal axis of accessory lever to accommodate human subjects of different body height, each accessory lever carrying a pedal carried by a structural beam supported by an elliptical assembly for use in generating an elliptical path of motion for pedal, beams on the right removed for clarity, two adjustable crank assemblies for use in adjusting angular movement of accessory levers to provide similar ranges of motion for limb joints of human subjects of different body height and limb length, two crossover assemblies for use in coupling movement of each leg to movement of the contralateral arm, two servo motors (or magnetic particle brakes) operating in torque mode for use in resisting reciprocating, angular movement of accessory levers and one secondary servo motor operating in torque mode for use in counteracting inertia of reciprocating mechanical parts and simulating an adjustable flywheel for use in simultaneously assessing the physical capacities and muscle compositions of all four limbs of a human subject.

FIG. 5 is a perspective view of a different embodiment of the present reciprocating dynamometer with four accessory levers, two accessory levers carrying handles and two accessory levers carrying pedals, each accessory lever carrying a handle carried by a structural beam supported by an actuator for use in adjusting the height of the pivotal axis of accessory lever to accommodate human subjects of different body height, each accessory lever carrying a pedal carried by a structural beam supported by an elliptical assembly for use in generating an elliptical path of motion for pedal, beams on the right removed for clarity, two adjustable crank assemblies for use in adjusting angular movement of accessory levers to provide similar ranges of motion for limb joints of human subjects of different body height and limb length, two crossover assemblies for use in coupling movement of each leg to movement of the contralateral arm, two servo motors (or magnetic particle brakes) operating in torque mode for use in resisting reciprocating, angular movement of accessory levers and one secondary servo motor operating in torque mode for use in counteracting inertia of reciprocating mechanical parts and simulating an adjustable flywheel for use in simultaneously assessing the physical capacities and muscle compositions of all four limbs of a human subject. This embodiment comprises all elements of the embodiment in FIG. 4 with the addition of two crossover assemblies.

This embodiment comprises a frame 502. Pivotally mounted to frame 502 are the first ends of four structural beams comprising two upper structural beams 506 and two lower structural beams 520, beams on the right removed for clarity. Each upper structural beam 506 has a first end 504 with a pivotal axis 510 and a second end 508. Pivotally mounted to second end 508 of upper structural beam 506 is an accessory lever 512 having a pivotal axis 514 and carrying a handle 516. Each lower structural beam 520 has a first end 518 with a pivotal axis 524 and a second end 522. Pivotally mounted to second end 522 of lower structural beam 520 is an accessory lever 526 having a pivotal axis 528 and carrying a pedal 530. Supporting second end 508 of each upper structural beam 506 is an actuator 532 for use in adjusting the height of pivotal axis 514 of accessory lever 512 to accommodate human subjects of different body height. Supporting second end 522 of each lower structural beam 520 is an elliptical assembly 534 for use in generating an elliptical path of motion for pedal 530.

Reciprocating, angular movements of all four accessory levers 512, 526 are operationally connected using four accessory tie rods 536 to four levers 538 operationally connected to four reaction torque transducers 540 operationally connected to two crossover assemblies 542, 544 operationally connected to two servo motors 554 and two crank drive levers 546, each crank drive lever 546 operationally connected using a crank tie rod 548 to an adjustable crank assembly 550, both adjustable crank assemblies operationally connected to a secondary servo motor 552 for use in counteracting inertia of reciprocating mechanical parts and simulating an adjustable flywheel. One crossover assembly 542 couples movement of the left arm to movement of the right leg. A second crossover assembly 544 couples movement of the right arm to movement of the left leg.

All four levers 538 are operationally connected to different reaction torque transducers 540 for use in distinguishing the torque input of each limb. Secondary servo motor 552 generates a secondary encoder signal is for use by computer processor to trigger capturing of data derived from timer signal, torque input signal and encoder signal and generating of brake output signal. Data is uploaded to a database for use in generating distinguishing plots of data for each arm, each leg, left-side of body, right-side of body, upper body, lower body and total body. The duration of a human physical capacity test is 15 seconds.

FIG. 6 is a perspective view of a different embodiment of the present reciprocating dynamometer with four levers, two levers carrying handles and two levers carrying pedals, each lever operationally connected to a reaction torque transducer operationally connected to a servo motor, each servo motor carrying a pedal rigidly mounted to a frame, each servo motor carrying a handle adjustably mounted to frame using an actuator for use in adjusting the height of the pivotal axis of lever to accommodate human subjects of different body height, frame on the right removed for clarity, all four servo motors operating in position mode and responsive to a position signal generated by a motion controller (see FIG. 8) operable to (1) simulate a master servo motor operating in velocity mode; (2) generate a position signal for use in adjusting and synchronizing opposing, angular movements of servo motors and corresponding levers for use in providing similar ranges of motion for limb joints of human subjects of different limb length; and (3) trigger capturing of data and generating of signals for use in simultaneously assessing physical capacities and muscle compositions of all four limbs of a human subject. This embodiment comprises all elements of the embodiment in FIG. 5 with the addition of a motion controller replacing the computer processor, secondary servo motor, adjustable crank assemblies, crank tie rods, crossover assemblies, accessory tie rods and accessory levers.

This embodiment comprises four levers 604, each lever 604 having a first end 602 with a pivotal axis 608 and a second end 606, second end 606 carrying a handle 610 or pedal 612. Adjustably mounted to first end 602 of lever 604 is a counterweight 614 for use in counterbalancing gravitational torque on lever 604. Operationally connected to lever 604 is a reaction torque transducer 616 generating a torque input signal responsive to magnitude of torque applied to lever 604, torque proportional to force applied by a human user to handle 610 or pedal 612 for use in moving lever 604 in a reciprocating, angular manner 632. Operationally connected to reaction torque transducer 616 is a servo motor 618 operating in position mode and generating an encoder signal responsive to angular position of servo motor 618, servo motor 618 responsive to a position signal generated by a motion controller (see FIG. 8). Two servo motors 620 carrying pedals 612 are rigidly mounted to a frame 622 having a common pivotal axis 624. Two servo motors 618, 626 carrying handles 610 are adjustably mounted using actuators 628 to a second aspect of the frame 630 having a common second pivotal axis 608, frame on the right removed for clarity.

Operationally connected to all four servo motors 618, 620, 626 is a motion controller (see FIG. 8) having a master timer, master timer generating a master timer signal, motion controller operable to: (1) simulate a master servo motor operating in velocity mode, master servo motor generating a master encoder signal responsive to master angular position of master servo motor, master angular position responsive to master angular velocity and master angular acceleration of master servo motor, master angular acceleration responsive to torque input signal and brake output signal, (2) generate position signal responsive to master encoder signal and body height input or limb length input of human user for use in adjusting and synchronizing opposing, angular movements of servo motors 618, 620, 626 and corresponding levers 604 for use in providing uniform angular movements 632 of levers from one movement cycle to the next and providing similar ranges of motion for limb joints of human subjects of different body height and limb length, and (3) use master encoder signal to trigger capturing of data derived from master timer signal, four torque input signals and four encoder signals and generating of brake output signal. Operationally connected to motion controller is a base computer (see FIG. 8).

Maximal angular movement of servo motors 618, 620, 626 is limited to 90 degrees by physical stops 634 as well as programmable, functional integrated safety stops for velocity, position and direction to prevent a system malfunction from harming a human user. In addition, "dead man" switches (not shown) are incorporated into the handles 610 and emergency stop switches (not shown) are located within easy reach of human user and base computer console.

Figure 7:
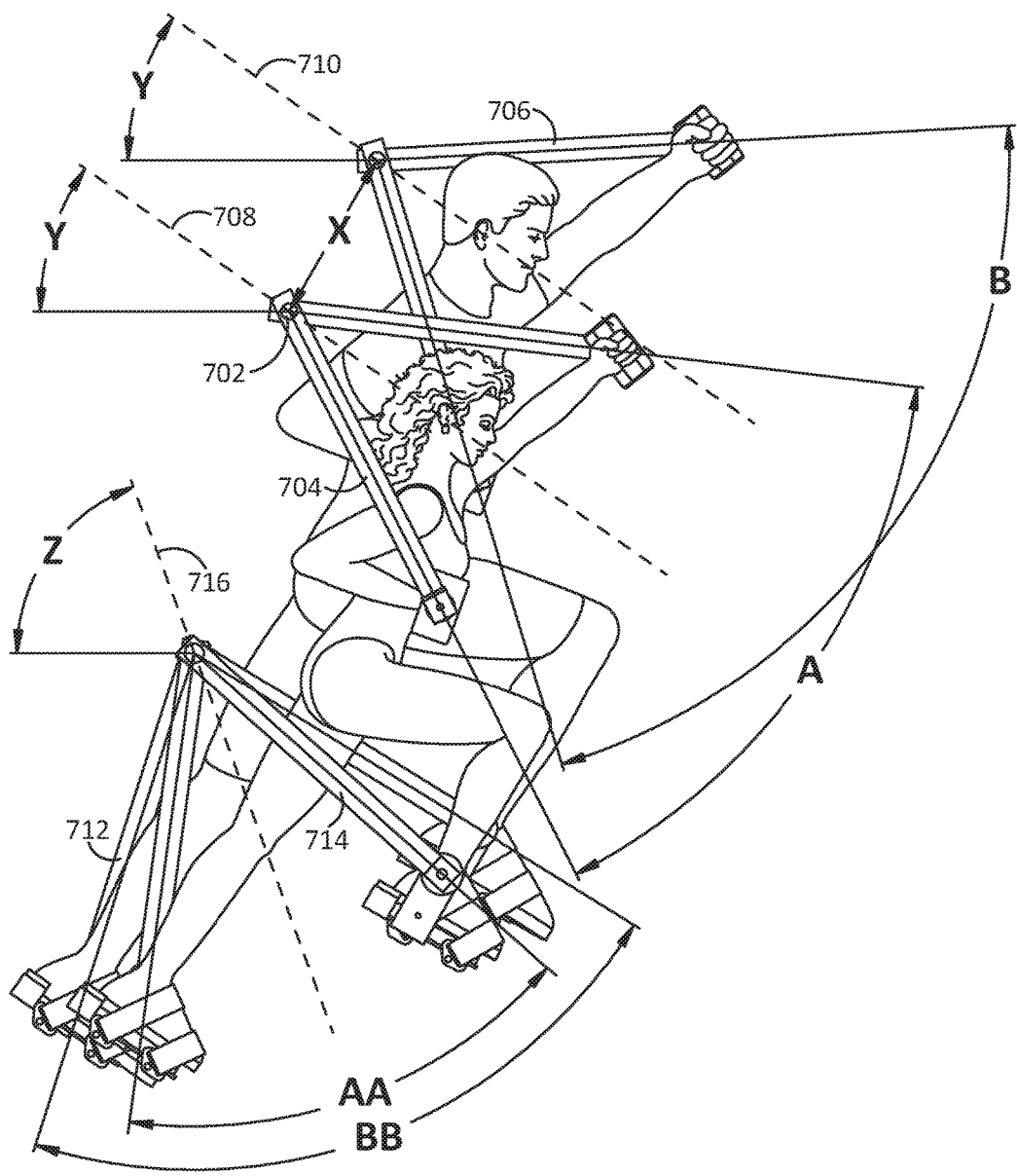
FIG. 7 is a profile view of a shorter female subject superimposed upon a taller male subject showing adjustment in angular movements of arm levers and leg levers to provide similar ranges of motion for limb joints of human subjects of different body height and limb length and adjustment in height of pivotal axes of arm levers relative to pivotal axes of leg levers to accommodate human subjects of different body height for use in simultaneously assessing the physical capacities and muscle compositions of all four limbs of a human subject.

FIG. 7 is a profile view of a shorter female subject superimposed upon a taller male subject showing adjustment in angular movements of arm levers and leg levers to provide similar ranges of motion for limb joints of human subjects of different body height and limb length and adjustment in height of pivotal axes of arm levers relative to pivotal axes of leg levers to accommodate human subjects of different body height for use in simultaneously assessing the physical capacities and muscle compositions of all four limbs of a human subject.

Arm lever axes 702 adjust upward or downward a distance of "X" to accommodate human subjects of different body height. Angular displacement of arm levers 704, 706 adjusts from "A" to "B" to accommodate human subjects of different body height or limb length, maintaining constant angle "Y" between centerlines 708, 710 of angular movement of arm levers 704, 706 and the horizon. Angular displacement of leg levers 712, 714 adjusts from "AA" to "BB" to accommodate human subjects of different body height or limb length while maintaining constant angle "Z" between centerline 716 of angular movement of leg levers and the horizon.

Figure 8:
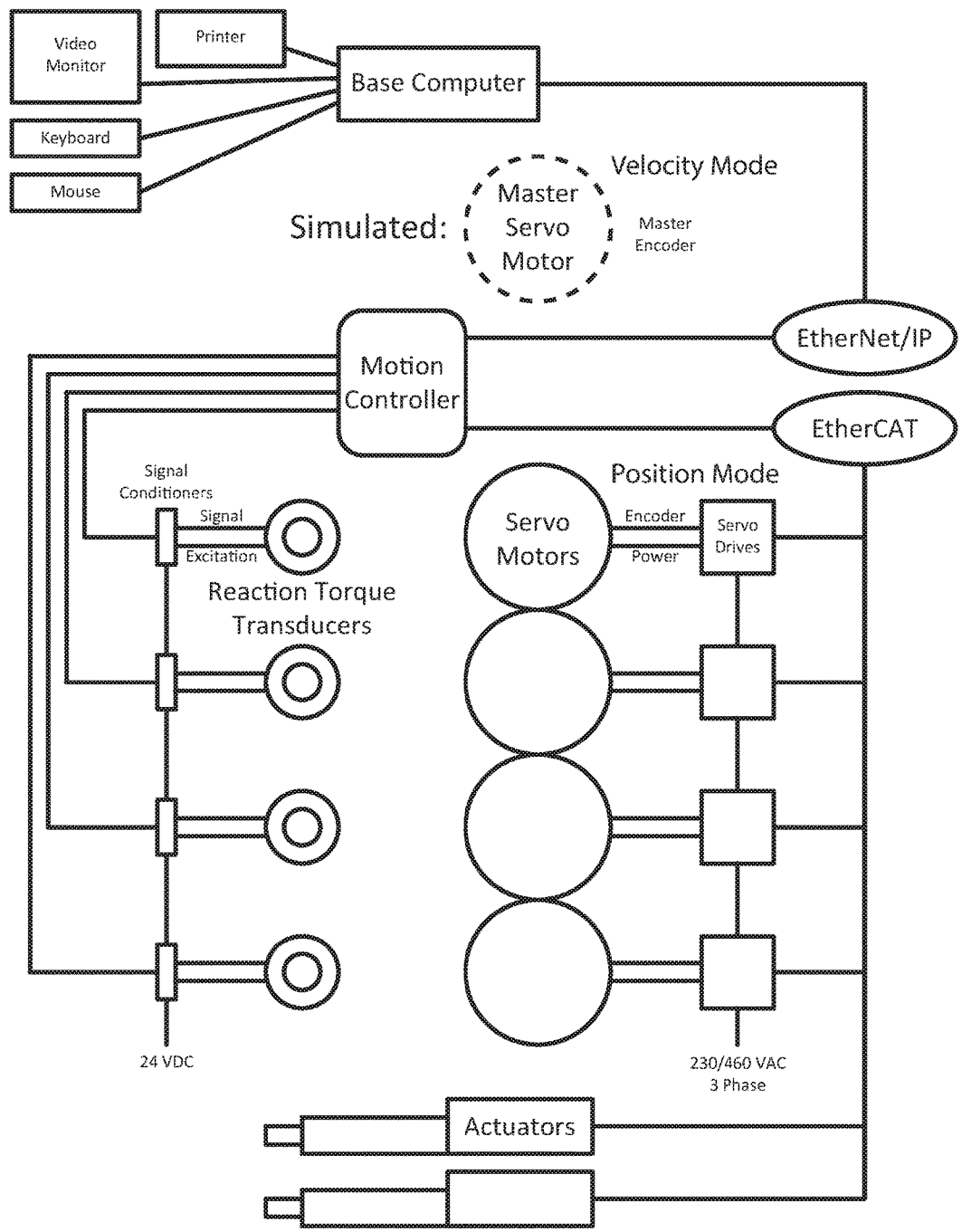
FIG. 8 is a diagram showing major electronic components for use by the embodiment in FIG. 6 of the present reciprocating dynamometer to assess human physical capacity and muscle composition.

FIG. 8 is a diagram showing major electronic components for use by the embodiment in FIG. 6 of the present reciprocating dynamometer to assess human physical capacity and muscle composition.

Figure 9:
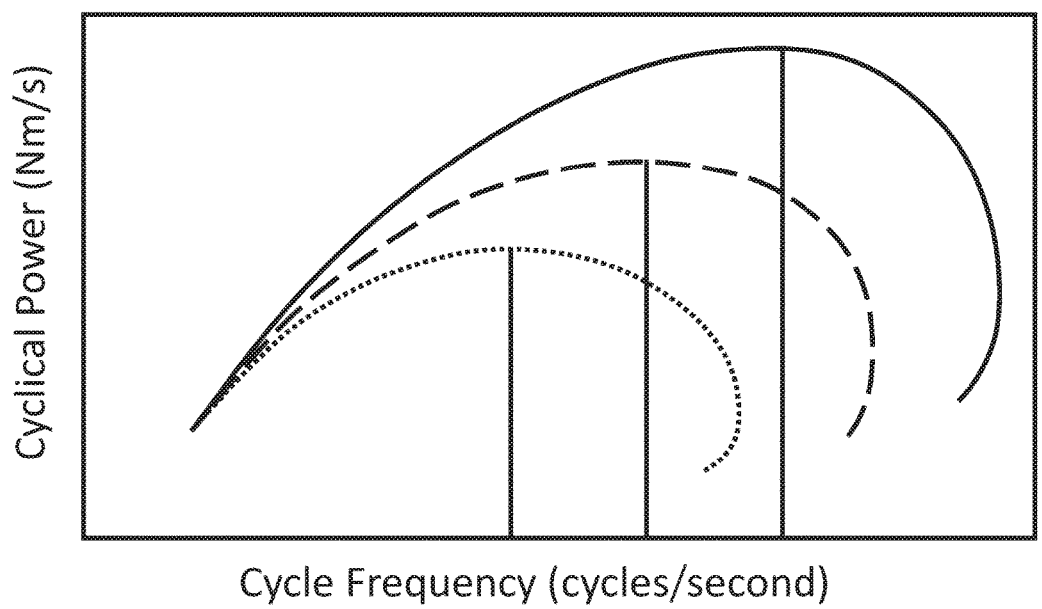
FIG. 9 is an overlay of three different plots of data generated by the present reciprocating dynamometer to assess human physical capacity and muscle composition showing cyclical power over cycle frequency of three athletes having similar height, weight, age, sex and muscle mass, but different muscle compositions.

FIG. 9 is an overlay of three different plots of data generated by the present reciprocating dynamometer to assess human physical capacity and muscle composition showing cyclical power over cycle frequency of three athletes having similar height, weight, age, sex and muscle mass, but different muscle compositions. The upper plot is that of a speed/power athlete, the middle plot that of a size/strength athlete and the lower plot that of an endurance athlete. Lack of strength, speed and power exercise or sustained, repetitive, aerobic, endurance training or malnutrition, disease, trauma, aging, etc., can result in a progressive loss of Type IIx muscle fibers followed by Type IIa muscle fibers, causing peak cyclical power on a plot of cyclical power over cycle frequency to shift lower and to the left over time.

It will be apparent to those knowledgeable about exercise equipment and human physical performance testing that many modifications and substitutions can be made to the foregoing description of embodiments without departing from the scope and spirit of the present disclosure which is defined by the appended claims.

What is claimed is:

1. A reciprocating dynamometer, comprising:
(a) at least one lever having a first end and a second end, said first end having a pivotal axis, said at least one lever configured to produce a reciprocating angular movement about said pivotal axis, said reciprocating angular movement being responsive to a torque applied to said second end of said at least one lever, said torque having a magnitude, said at least one lever having an angular position relative to said reciprocating angular movement;
(b) means for generating a torque input signal responsive to said magnitude of said torque applied to said second end of said at least one lever, said means for generating a torque input signal being operably connected to said at least one lever;
(c) a primary rotary encoder connected to said first end of said at least one lever, wherein said primary rotary encoder is an absolute rotary encoder, said absolute rotary encoder configured to generate an absolute rotary encoder signal responsive to said angular position of said at least one lever;
(d) a magnetic particle brake connected to said first end of said at least one lever, said magnetic particle brake configured to apply resistance to said reciprocating angular movement of said at least one lever in response to a brake output signal, said resistance being adjustable in magnitude;
(e) a crank arm having a first end and a second end, said first end having a rotational axis, said crank arm configured to produce a rotating movement about said rotational axis, said crank arm having an angular position relative to said rotating movement;
(f) a tie rod connected between said at least one lever and said second end of said crank arm, whereby said reciprocating angular movement of said at least one lever is transmitted by said tie rod to produce said rotating movement of said crank arm;
(g) a secondary rotary encoder connected to said first end of said crank arm, said secondary rotary encoder configured to generate a secondary rotary encoder signal responsive to said angular position of said crank arm; and (h) a base computer having a timer configured to generate a timer signal, said base computer operably connected to said means for generating a torque input signal, said absolute rotary encoder, said magnetic particle brake and said secondary rotary encoder, said base computer configured to use said secondary rotary encoder signal to trigger capturing and recording of data derived from said timer signal, said torque input signal and said absolute rotary encoder signal and generating said brake output signal, said base computer further configured to compute a cyclical moving average of power and a cycle frequency.

* * * * *